United States Patent [19]

Mori et al.

[11] Patent Number: 5,648,554
[45] Date of Patent: Jul. 15, 1997

[54] METHOD FOR PRODUCING ALDEHYDES

[75] Inventors: Tomoyuki Mori; Masaki Takai; Tomohiko Inoue, all of Okayama, Japan

[73] Assignee: Mitsubishi Chemical Corporation, Tokyo, Japan

[21] Appl. No.: 632,356

[22] Filed: Apr. 10, 1996

[30] Foreign Application Priority Data

Apr. 12, 1995 [JP] Japan .................................. 7-086906

[51] Int. Cl.$^6$ .................................................. C07C 45/50
[52] U.S. Cl. .................................... 568/454; 568/451
[58] Field of Search ........................................ 568/451, 454

[56] References Cited

U.S. PATENT DOCUMENTS

| | | |
|---|---|---|
| 4,496,768 | 1/1985 | Dennis et al. . |
| 4,496,769 | 1/1985 | Dennis et al. . |
| 4,769,498 | 9/1988 | Billig et al. .............................. 568/454 |
| 5,138,101 | 8/1992 | Devon . |
| 5,202,297 | 4/1993 | Lorz et al. . |
| 5,254,741 | 10/1993 | Lorz et al. . |
| 5,288,918 | 2/1994 | Maher et al. . |
| 5,364,950 | 11/1994 | Babin et al. .................................. 556/2 |
| 5,414,138 | 5/1995 | Omatsu et al. . |

FOREIGN PATENT DOCUMENTS

| | | |
|---|---|---|
| 53 68709 | 6/1978 | Japan . |
| 56 2994 | 1/1981 | Japan . |

OTHER PUBLICATIONS

Patent Abstracts of Japan, JP-A-51 11745, (with GB 1 502 339) (1981).

Encyclopedia of Chemical Technology; vol. 18; Fourth edition; pp. 664–666; 1996 1996.

*Primary Examiner*—C. Warren Ivy
*Assistant Examiner*—Sreeni Padmanabhan
*Attorney, Agent, or Firm*—Oblon, Spivak, McClelland, Maier & Neustadt, P.C.

[57] ABSTRACT

A method for producing aldehydes, which comprises reacting an olefinic unsaturated compound with carbon monoxide and hydrogen in a liquid phase in the presence of a Group 8 metal-phosphite complex catalyst, wherein a reaction product solution containing the complex catalyst and a high boiling by-product, obtained by the reaction, is intimately contacted with an extraction solution containing a polar solvent, to have either the complex catalyst or the high boiling by-product extracted selectively, followed by phase separation to separate a layer of the extraction solution from a layer of the reaction product solution.

13 Claims, No Drawings

METHOD FOR PRODUCING ALDEHYDES

BACKGROUND OF THE INVENTION

1. Field of the Invention

The present invention relates to a method for producing aldehydes by subjecting an olefinic unsaturated compound to a hydroformylation reaction in the presence of a Group 8 metal-phosphite complex catalyst.

2. Discussion of Background

A process for producing aldehydes which comprises reacting an olefinic unsaturated compound with carbon monoxide and hydrogen in the presence of a Group 8 metal complex catalyst, is widely practiced on an industrial scale. As a catalyst for this hydroformylation reaction, it is common to employ a complex catalyst having a Group 8 metal such as rhodium modified with a ligand such as a trivalent phosphorus compound. In order to improve the activity or selectivity for the hydroformylation reaction, various ligands have been studied. For example, Japanese Examined Patent Publication No. 10730/1970 discloses that a rhodium catalyst modified with a trivalent phosphorus ligand such as a triaryl phosphine or a triaryl phosphite, is effective.

Among various catalysts, a catalyst modified with a phosphite ligand is known to show a high catalytic activity and excellent selectivity in the hydroformylation reaction.

However, as disclosed in Japanese Unexamined Patent Publication No. 51229/1984, with a phosphite ligand such as triphenyl phosphite, it is known that the ligand is relatively quickly decomposed in the hydroformylation reaction system, whereby the catalytic activity will decrease, and it is therefore necessary to continuously supplement the phosphite ligand. Accordingly, for the purpose of not only improving the activity and selectivity of the catalyst but also minimizing the decrease of the catalytic activity due to the loss of the phosphite ligand, various phosphite ligands have been proposed.

For example, Japanese Unexamined Patent Publications No. 51228/1984 and No. 290551/1992 disclose that the stability of the phosphite itself is improved in order to suppress the decomposition of the phosphite ligand. Further Japanese Unexamined Patent Publication No. 156636/1985 discloses a method wherein a tertiary amine is present in the hydroformylation reaction zone to stabilize the phosphite ligand.

Further, with respect to a technique for separating the catalyst, Japanese Unexamined Patent Publication No. 49190/1975 discloses an adsorption method, Japanese Unexamined Patent Publication No. 122948/1982 discloses a precipitation method, and Japanese Unexamined Patent Publication No. 231435/1990 discloses a membrane separation method. Japanese Unexamined Patent Publication No. 2994/1981 discloses a method wherein a catalyst solution obtained by a hydroformylation reaction using a rhodium-phosphine complex catalyst, is contacted with a paraffin or a cycloparaffin and a polar organic solvent, followed by separation into two phases, so that the majority of the rhodium complex can be obtained in the polar organic solvent phase. However, industrially, it is most common to employ distillation for the separation.

As a reaction medium for a usual liquid phase hydroformylation reaction, it is common to employ not only an inert solvent such as an aromatic hydrocarbon but also a high boiling by-product produced by a condensation reaction of an aldehyde product. When either medium is employed, the high boiling by-product will be formed as time passes and will gradually accumulate unless it is withdrawn. The accumulation of such a high boiling by-product brings about not only a mass balance problem but also a necessity to withdraw a part of the high boiling by-product continuously or intermittently out of the system, since it sometimes becomes poisonous to the catalyst.

On the other hand, in a case where a Group 8 metal complex catalyst is used on an industrial scale, it is necessary to recycle the catalyst continuously, since the Group 8 metal is expensive. Accordingly, when a part of the high boiling by-product is purged as described above, it is necessary to selectively withdraw a high boiling by-product in order to minimize the loss of the Group 8 metal complex catalyst. As a separation method for withdrawing such a high boiling by-product, distillation has been commonly used in the conventional phosphine type process.

When a commonly employed aromatic hydrocarbon solvent such as benzene, toluene or xylene is used as the solvent for a hydroformylation reaction, the boiling point of the catalyst solution becomes very high. Accordingly, steam distillation may sometimes be used as a means for lowering the temperature of the distillation still, when distillation is employed for the separation of the high boiling by-product and the catalyst component. The temperature of such a distillation still will be 120° C. or as high as 170° C. or higher in some cases.

When an organic phosphine compound such as triphenyl phosphine is used as the ligand of the Group 8 metal catalyst in the hydroformylation reaction, there will usually be no problem even under a high temperature condition as mentioned above. Whereas, when a phosphite type ligand which exhibits a high activity and high selectivity in the reaction as compared with a phosphine type ligand, is to be used, such a phosphite is substantially inferior in the thermal stability to the phosphine. Accordingly, in a method for separating a high boiling by-product by distillation at a high temperature as mentioned above, rapid decomposition of the phosphite takes place. Thus, it has been practically impossible to use a phosphite for an industrial operation.

Further, in a case where steam distillation is used to lower the temperature, vigorous decomposition of the phosphite takes place, since the phosphite is highly susceptible to hydrolysis. As the phosphite is highly susceptible to hydrolysis, it has been believed that water in the process accelerates decomposition of the phosphite, and the water should be reduced as far as possible. On the other hand, as disclosed in Japanese Unexamined Patent Publication No. 199728/1994, presence of a small amount of water is advantageous. Even then, it is described that to add too much water, e.g. water in such an amount that an aqueous phase and an organic phase are separated during the extraction separation operation, is undesirable. Namely, in the prior art, it has been difficult to separate the complex catalyst or the high boiling by-product by an aqueous extraction operation in the phosphite type process.

Accordingly, to utilize the phosphite type ligand having higher performance than the phosphine type ligand industrially, it has been an important object to establish a method whereby decomposition of the phosphite ligand is suppressed and a part of the high boiling by-product is withdrawn while minimizing the loss of the complex catalyst.

SUMMARY OF THE INVENTION

The present inventors have conducted extensive studies to accomplish the object and as a result, have found it possible to separate the complex catalyst or the high boiling by-product selectively without decomposing the phosphite ligand, by intimately contacting a reaction product solution of hydroformylation employing a Group 8 metal-phosphite complex catalyst with an extraction solution containing a polar solvent. The present invention has been accomplished on the basis of this discovery.

Namely, the present invention provides a method for producing aldehydes, which comprises reacting an olefinic unsaturated compound with carbon monoxide and hydrogen in a liquid phase in the presence of a Group 8 metal-phosphite complex catalyst, wherein a reaction product solution containing the complex catalyst and a high boiling by-product, obtained by the reaction, is intimately contacted with an extraction solution containing a polar solvent, to have either the complex catalyst or the high boiling by-product extracted selectively, followed by phase separation to separate a layer of the extraction solution from a layer of the reaction product solution.

DETAILED DESCRIPTION OF THE PREFERRED EMBODIMENTS

Now, the present invention will be described in detail.

In the present invention, the reaction product solution obtained by the hydroformylation reaction contains at least (i) a high boiling by-product, (ii) a complex catalyst containing a Group 8 metal and a phosphite compound, and (iii) a reaction medium. The present invention is directed to a method wherein this reaction product solution is intimately contacted with an extraction solution containing a polar solvent to have either the complex catalyst or the high boiling by-product transferred selectively to the extraction solution side, followed by separation into two phases i.e. a layer of the reaction product solution and a layer of the extraction solution.

In the present invention, the following method (I) or (II) may be mentioned as the method of having either the complex catalyst or the high boiling by-product extracted selectively.

(I) A method in which the type of the extraction solution is selected so that the high boiling by-product is selectively extracted, and the extraction rate of the catalyst components such as the catalytically active Group 8 metal-phosphite complex and an excessive phosphite compound, can be minimized. Then, the reaction product solution layer containing the catalyst components, can be recycled to the hydroformylation reactor, whereby the loss of the catalyst from the hydroformylation production system can be minimized.

(II) A method wherein the type of the extraction solution is selected so that the complex catalyst is selectively extracted. Then, the catalyst components can be transferred from the extraction solution layer containing the complex catalyst to a non-porous layer by a method such as reverse extraction and then returned to the hydroformylation reactor. From the reaction product solution layer containing the high boiling by-product, the solvent for reaction will be recovered by a usual method such as distillation and reused.

The hydroformylation reaction product solution is usually preliminarily subjected to separation of the aldehyde product by a conventional method such as distillation before it is subjected to the extraction operation. However, the reaction product solution may directly be subjected to the extraction operation. Further, the entire amount of the reaction product solution may not necessarily be subjected to the extraction operation. In some cases, a part thereof may be withdrawn for the extraction operation.

The extraction solution may contain various polar solvents which are capable of establishing phase separation from the hydroformylation reaction product solution. Further, the polar solvents themselves may not phase-separated from the hydroformylation reaction product solution, so long as they are capable of establishing phase separation, for example, when mixed with water. Namely, the extraction solution may comprise a plurality of components. Such polar solvents include, for example, water; ketones such as acetone, methyl ethyl ketone, 2-pentanone, 3-pentanone and diethyl ketone; alcohols such as propanol and butanol; ethers such as diethyl ether, dipropyl ether, dioxane, diglyme and triglyme; nitriles such as acetonitrile and propionitrile; amides such as dimethylformamide, diethylformamide, acetamide, dimethylacetamide and N-methylpyrrolidone; diols such as ethylene glycol, propane diol and butane diol; lower carboxylic acids; and compounds having two or more functional groups, such as diethylene glycol monomethyl ether and 2-methoxyethanol. Among these solvents, those which are capable of selectively extracting only the high boiling by-product without extracting the complex catalyst, are preferred. As such solvents, alkanols having up to three carbon atoms, particularly primary alcohols such as methanol and ethanol, may preferably be used to obtain particularly good results. Further, similarly good results can be obtained by using carboxylic acids such as formic acid and acetic acid, diols such as ethylene glycol and butane diol, or amides such as diethylformamide and N-methylpyrrolidone.

Conversely, solvents which are capable of selectively extracting only the complex catalyst without extracting the high boiling by-product, are also preferred. For example, alkylamines such as triethylamine and trioctylamine, alkanol amines such as methanol amine and ethanol amine, and cyclic amines such as pyridine, may be mentioned. Further, nitriles such as acetonitrile, ketones such as acetone and methyl ethyl ketones and ethers such as dioxane, may also be preferably employed.

As mentioned above, presence of water in the extraction solution is not necessarily required, so long as the extraction solution is capable of being phase-separated from the hydroformylation reaction product solution. However, in many cases, presence of water is effective not only for phase separation but also for providing an extraction efficiency. Relative amounts of the polar solvent and the water constituting the extraction solution substantially change depending upon the type of the high boiling by-product or the complex catalyst to be recovered and the solvent for reaction used. However, usually, the volume ratio of the polar solvent to the water is within a range of from 20:1 to 1:20, preferably from 5:1 to 1:1.

Partition of the complex catalyst or the high boiling by-product between the hydroformylation reaction product solution and the extraction solution is an equilibrium process, and the relative volumes of the extraction solution and the reaction product solution in the extraction operation, are determined depending upon the solubility of the complex catalyst or the high boiling by-product in the solution used, the content of the polar solvent in the extraction solution and the amount of the complex catalyst or the high boiling by-product to be separated. For example, when the high boiling by-product is to be extracted, if the high boiling by-product to be separated shows high solubility in the extraction solution and is present at a relatively low concentration in the reaction product solution, it is possible to practically extract the high boiling by-product by using the extraction solution in a relatively small volume ratio to the reaction product solution. Further, as the concentration of the high boiling by-product becomes high, it is usually required to increase the ratio of the extraction solution to the reaction product solution for practically extracting the high boiling by-product from the reaction product solution. When the high boiling by-product shows relatively low solubility in the extraction solution, the relative volume of the extraction solution will have to be increased. Usually, the volume ratio of the extraction solution to the reaction product solution may be changed within a range of from 10:1 to 1:10. However, by carefully selecting the ratio of the reaction product solution to the extraction solution, a range of from 1:1 to 1:4 may be employed among the above volume ratio for separation of most of high boiling by-products.

The same is true for the extraction of the complex catalyst.

With respect to the extraction temperature, there is no merit in employing a temperature higher than the hydroformylation reaction temperature (e.g. a temperature of from 70° to 125° C.), and excellent results can be obtained by employing an extraction temperature lower than the hydroformylation reaction temperature. It is practically preferred to conduct this extraction operation within a temperature range of from 10° to 60° C., more preferably from 10° to 45° C., in view of the extraction efficiency, the equilibrium-reaching temperature and the energy problem. However, the temperature is not limited to such a range, when some reaction takes place during the extraction. For example, during the extraction, the high boiling by-product may be changed by a reaction into such a form that can readily be extracted into the extraction solution layer. In such a case, there may be the optimum temperature for the particular reaction.

The time for contacting the hydroformylation reaction product solution with the extraction solution, i.e. the time before the phase separation, depends on the rate until the two-phases reach the equilibrium condition. Practically, such a time may be varied from within one minute to a long period of time exceeding three hours.

The extraction process in the present invention is an equilibrium process of a specific compound dissolved in the two separate liquid phases. The efficiency of this extraction process can be measured by a partition coefficient Kp of compound X, which is defined as follows:

$$Kp = \frac{\text{Concentration } X \text{ in the extraction solution after extraction}}{\text{Concentration of } X \text{ in the reaction product solution after extraction}}$$

When the high boiling by-product is partitioned between the hydroformylation reaction product solution and the extraction solution by the extraction process of the present invention, the Kp value of the complex catalyst can be suppressed to a level of at most 0.2, preferably at most 0.06, more preferably at most 0.03, although it depends on the economical nature of the extraction process. In this case, the higher the Kp value of the high boiling by-product, the better. If this Kp value is high, the extraction efficiency will be high, and the amount of the extraction solution required will be small. The same is true in the case where the complex catalyst is subjected to partition. Further, the lower the Kp value of the solvent for reaction, the better, in that the loss of the solvent can be reduced.

The Group 8 metal-phosphite complex catalyst may be formed in the hydroformylation reaction system by supplying a Group 8 metal source and a phosphite compound directly to the hydroformylation reactor. Otherwise, the complex catalyst may be prepared beforehand by reacting a Group 8 metal source together with carbon monoxide, hydrogen and a phosphite compound in a solvent under a high temperature-pressure condition outside the reactor. The solvent to be used for the preparation of the catalyst is usually selected from the solvents for the reaction which will be described hereinafter. However, such a solvent may not necessarily be the same solvent as the solvent for reaction. With respect to the preparation conditions, the pressure is usually from atmospheric pressure to 100 kg/cm$^2$G, and the temperature is from room temperature to 150° C.

The Group 8 metal source for the complex catalyst may, for example, be a ruthenium compound such as $Ru_3(CO)_{12}$, $Ru(NO_3)_3$, $RuCl_2(Ph_3P)_4$ or $Ru(acac)_3$, a palladium compound such as $PdCl_2$, $Pd(OAc)_2$, $Pd(acac)_2$, $PdCl_2(COD)$ or $PdCl_2(Ph_3P)_2$, an osmium compound such as $OS_3(CO)_{12}$ or $OsCl_3$, an iridium compound such as $Ir_4(CO)_{12}$ or $IrSO_4$, a platinum compound such as $K_2PtCl_4$, $PtCl_2(PhCN)_2$ or $Na_2PtCl_6 \cdot 6H_2O$, a cobalt compound such as $CoCl_2$, $CO(NO_3)_2$, $Co(OAc)_2$ or $CO_2(CO)_8$, a rhodium compound such as a Rh metal supported on a carrier such as alumina, silica or active carbon, an inorganic salt such as $RhCl_3$ or $Rh(NO_3)_3$, an organic salt such as $Rh(OAc)_3$ or $Rh(OCOH)_3$, a rhodium oxide such as $Rh_2O_3$, a chelate compound such as $Rh(acac)(CO)_2$, an inorganic or organic salt of rhodium such as sodium chlororodate or potassium chlororodate, or a rhodium complex compound such as $[Rh(OAc)(COD)]_2$, $Rh_4(CO)_{12}$, $Rh_6(CO)_{16}$, $\mu,\mu'$-$Rh_2Cl_2(CO)_4$, $RhH(CO)(Ph_3P)_3$, $[Rh(OAc)(CO)_2]_2$, $[RhCl(COD)]_2$ or $[Rh(\mu$-$S(t$-$Bu))(CO)_2]_2$ (here, acac represents an acetylacetonate group, Ac represents an acetyl group, COD represents cyclooctadiene, and Ph represents a phenyl group). It is particularly preferred to employ a rhodium compound among them.

The phosphite ligand which may be complexed with the Group 8 metal and a free phosphite ligand may be any phosphite compound such as a triaryl phosphite, a trialkyl phosphite or an arylalkyl phosphite. Further, a bisphosphite or polyphosphite compound having a combination thereof in the same molecule, may also be used.

Triphenyl phosphite or the like is likely to readily react with an aldehyde compound even at room temperature, whereby the ligand will be lost. Therefore, preferred compounds for the purpose of the present invention among the phosphite compounds, may be phosphite compounds having low reactivity with aldehydes or water and having improved stability, for example, by steric hindrance in the molecular structures. Such phosphite compounds having high stability may be classified into the following two groups of compounds. Namely, the first group of compounds are phosphite compounds having no cyclic structure containing a phosphorus atom in their molecules, and the second group of compounds are phosphite compounds having cyclic structures containing a phosphorus atom in their molecules.

Firstly, as the phosphite compound having no cyclic structure containing a phosphorus atom in its molecule, it is referred to employ the one wherein at least one alcohol component of the phosphite compound has a hydroxyl group directly bonded to an aromatic ring and is an aromatic alcohol having a hydrocarbon substituent on a carbon atom adjacent to the carbon atom to which said hydroxyl group is bonded. For example, a phosphite compound represented by the following formula (1) may be mentioned:

  (1)

wherein each of R₁, R₂ and R₃ which are independent of one another, is an organic group, and at least one of them is a substituted phenyl group of the following formula (2):

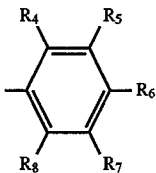 (2)

wherein R₄ is a group of the formula C(R₉)(R₁₀)(R₁₁) or an aryl group which may have a substituent, each of R₉, R₁₀ and R₁₁ which may be the same or different, is a hydrogen atom, a hydrocarbon group or a fluorinated hydrocarbon group, and each of R₅, R₆, R₇ and R₈ which may be the same or different, is a hydrogen atom or an organic group.

Preferred is the one wherein R₄ in the formula (2) is bulky as a whole as being an isopropyl group or a higher alkyl group. Specific examples of such a compound include diphenyl(2,4-di-t-butylphenyl)phosphite, diphenyl(2-isopropylphenyl)phosphite and bis(2-t-butyl-4-methylphenyl)phenyl phosphite.

Among them, a compound of the formula (1) wherein all of R₁, R₂ and R₃ are substituted phenyl groups of the formula (2), is further preferred. Specific examples of such a compound include tris(2,4-di-t-butylphenyl) phosphite, tris(2-t-butyl-4-methylphenyl)phosphite, tris(2-t-butyl-4-methoxyphenyl)phosphite, tris(o-phenylphenyl) phosphite, and tris(o-methylphenyl) phosphite.

As another preferred example of the phosphite compound having no cyclic structure containing a phosphorus atom in its molecule, a phosphite compound of the following formula (1') may be mentioned:, a phosphite compound of the following formula may, for example, be mentioned:

P(OR₁)(OR₂)(OR₃)  (1')

wherein each of R₁, R₂ and R₃ which are independent of one another, is an organic group, and at least one of them is a substituted-2-naphthyl group of the following formula (3):

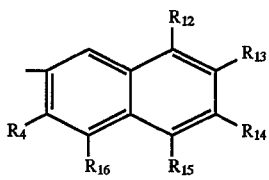 (3)

wherein R₄ is a group of the formula C(R₉)(R₁₀)(R₁₁) or an aryl group which may have a substituent, each of R₉, R₁₀ and R₁₁ which may be the same or different, is a hydrogen atom, a hydrocarbon group or a fluorinated hydrocarbon group, and each of R₁₂, R₁₃, R₁₄, R₁₅ and R₁₆ which may be the same or different, is a hydrogen atom or an organic group.

Preferred is the one wherein R₄ in the formula (3) is bulky as a whole as being an isopropyl group or a higher alkyl group. As a specific example of such a compound, diphenyl (3,6-di-t-butyl-2-naphthyl)phosphite may be mentioned.

Among them, more preferred is a compound of the formula (1') wherein each of R₁, R₂ and R₃ which may be the same or different, is a 2-naphthyl group which may be substituted, and substituent R₄ of at least one 2-naphthyl group among R₁, R₂ and R₃ is as defined by the above formula (3). As a specific example of such a compound, bis(2-naphthyl)(3,6-di-t-butyl-2-naphthyl) phosphite may be mentioned.

Among them, more preferred is a compound of the formula (1') wherein at least one of R₁, R₂ and R₃ is a substituted-2-naphthyl group of the formula (3), and the rest being a substituted phenyl group of the formula (2).

Specific examples of such a compound include bis(3,6-di-t-butyl-2-naphthyl)(2,4-di-t-butylphenyl)phosphite, and bis(3,6-di-t-butyl-2-naphthyl)(2-t-butylphenyl) phosphite.

Among them, most preferred is a compound of the formula (1') wherein all of R₁, R₂ and R₃ are substituted-2-naphthyl groups of the formula (3).

Specific examples of such a compound include tris(3,6-di-t-butyl-2-naphthyl)phosphite, and tris(3,6-di-t-amyl-2-naphthyl)phosphite.

Another example of a preferred ligand is a phosphite compound of the formula (1') wherein each of R₁ and R₂ is a 2-naphthyl group which is substituted by hydrocarbon groups which may be the same or different, at least at its 3-, 6- and 8-positions and which may have another substituents, and R₃ is an alkyl group, a cycloalkyl group or a phenyl group which may have a substituent only at the m-position and/or p-position. Specific examples of such a compound include bis(3,6,8-tri-t-butyl-2-naphthyl)phenylphosphite, and bis(3,6,8-tri-t-butyl-2-naphthyl)(p-tolyl)phosphite.

Among phosphite compounds having no cyclic structure containing a phosphorus atom in their molecules as the phosphite compounds useful for the present invention, another example of a preferred compound may be a bisphosphite or polyphosphite compound of the following formula (4):

A₁[—O—P(OR₁₇)OR₁₈)]ₙ  (4)

wherein each of R₁₇ and R₁₈ which may be the same or different, is an aromatic hydrocarbon group, provided that at least one of the aromatic hydrocarbon groups has a hydrocarbon group on a carbon atom adjacent to the carbon atom bonded to an oxygen atom, A₁ is a n-valent organic group containing a partial structure of an aliphatic, alicyclic or aromatic hydrocarbon which may have a substituent, the respective [—O—P(OR₁₇)(OR₁₈)] groups may be the same or different, and n is an integer of from 2 to 4.

It is preferred to employ a phosphite compound of the formula (4) wherein at least one of R₁₇ and R₁₈ is a substituted phenyl group of the above formula (2), or a substituted 2-naphthyl group of the above formula (3).

It is more preferred to employ a phosphite compound of the formula (4) wherein each of R₁₇ and R₁₈ is a substituted phenyl group of the above formula (2). Specific examples of such a compound include compounds of the following formulas:

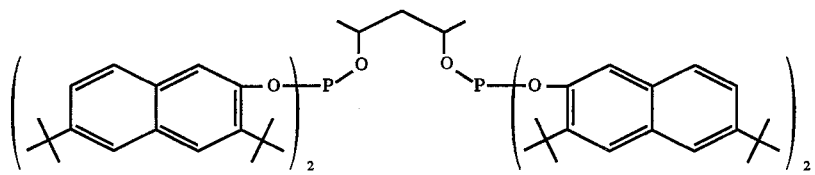

-continued
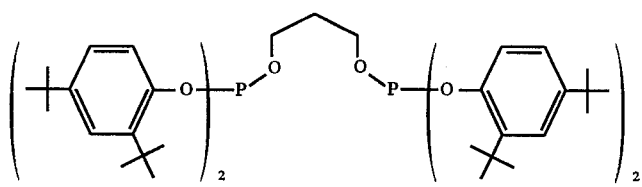
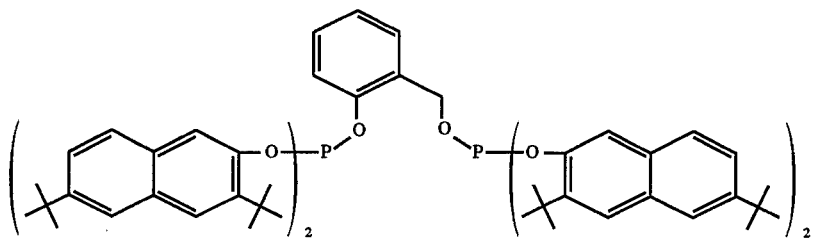
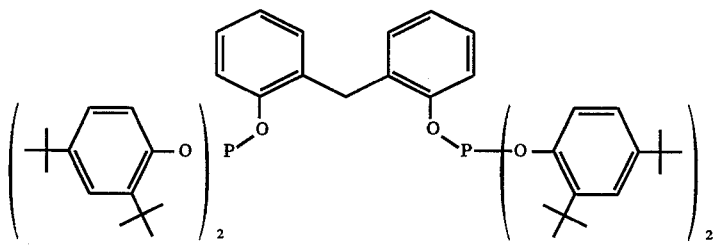
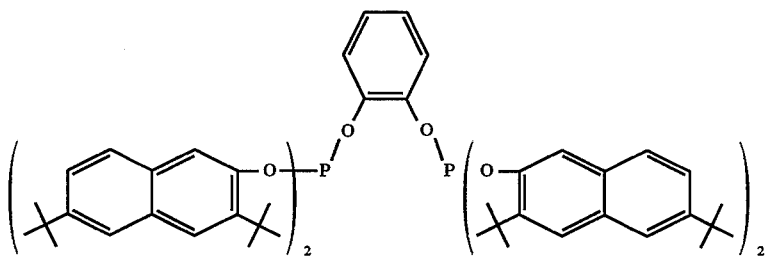
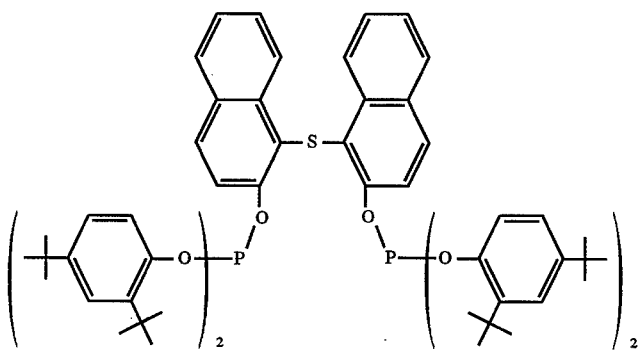
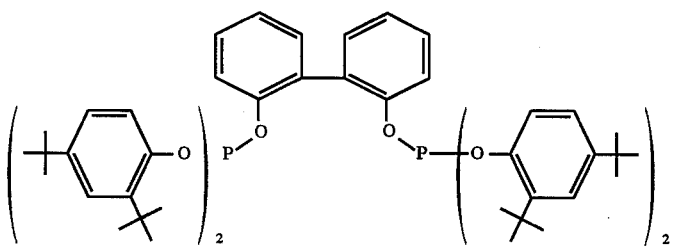
As another group of compounds among the phosphite compounds useful in the present invention, i.e. as the phosphite compounds having a cyclic structure containing a phosphorus atom in their molecules, phosphite compounds of the following formula (5) may, for example, be mentioned:

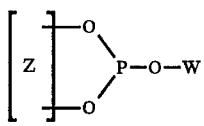

(5)

wherein Z is a bivalent organic group, and W is a substituted or unsubstituted monovalent hydrocarbon group.

As a typical organic group for Z in the formula (5), a bivalent aliphatic group or a bivalent aromatic group may for example, be mentioned. The bivalent aliphatic group may, for example, be an alkylene group, an alkyleneoxyalkylene group, an alkylene-NX-alkylene group), (wherein X is hydrogen or a monovalent hydrocarbon group), an alkylene-S-alkylene group of a cycloalkylene group. The bivalent aromatic group may, for example, be an arylene group, an arylenealkylene group, an arylenealkylenearylene group, an arylenooxyarylene group, an aryleneoxyalkylene group, an arylene-NX-arylene group, an arylene-NX-alkylene group (wherein X is hydrogen or a monovalent hydrocarbon group), an arylene-S-alkylene group, and an arylene-S-arylene group.

Among these phosphite compounds, an example of a preferred compound may be a bicyclic or polycyclic phosphite compound containing a trivalent organic group Z' as shown by the following formula (6), just like a combination of a bivalent organic group Z and a monovalent hydrocarbon group W in the formula (5).

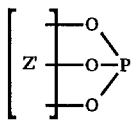

(6)

Specific examples of such a compound include 4-methyl-2,6,7-trioxa-1-phosphabicyclo[2.2.2]octane, 4-ethyl-2,6,7-trioxa-1-phosphabicyclo[2.2.2]octane, ethoxymethyl-2,6,7-trioxa-1-phosphabicyclo[2.2.2]octane, and 4-acetoxymethyl-2,6,7-trioxa-1-phosphabicyclo[2.2.2]octane.

Another example of a preferred phosphite compound among compounds of the formula (5) may be a phosphite compound of the following formula (7):

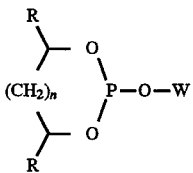

(7)

wherein each R is hydrogen, an alkyl group or a cycloalkyl group, which may have a substituent, and two R may be the same or different from each other, and n is an integer of from 0 to 4.

R in the formula (7) may, for group, an ethyl group, a phenyl group, a tolyl group, a benzyl group, a naphthyl group, a hydroxymethyl group, a hydroxyethyl group, or a trifluoromethyl group.

It is preferred to employ a phosphite compound of the formula (5) wherein W is an aryl group having a hydrocarbon group on a carbon atom adjacent to the carbon atom bonded to an oxygen atom, as represented by the formula (2) or (3).

Another example of a preferred phosphite compound may be a phosphite compound of the following formula (8):

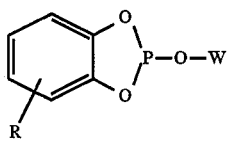

(8)

wherein W is a substituted or unsubstituted monovalent hydrocarbon group, R is a hydrocarbon group, and R may form a condensed aromatic ring which is condensed with the benzene ring.

R in the formula (8) may, for example, be an alkyl group, a cycloalkyl group, an alkoxy group, an acyl group, an acyloxy group or an aryl group which may have a substituent, or R is a condensed aromatic ring such as a naphthyl ring condensed with the benzene ring.

It is more preferred to employ a phosphite compound of the formula (8) wherein W is an aryl group having a hydrocarbon group on a carbon atom adjacent to the carbon atom bonded to an oxygen atom, as shown by the formula (2) or (3).

Another example of a preferred phosphite among compounds of the formula (5) may be a phosphite compound of the following formula (9):

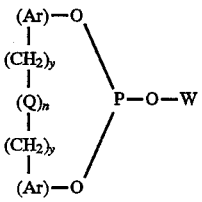

(9)

wherein each of two Ar which may be the same or different, is a substituted or unsubstituted arylene group, y is 0 or 1, Q is a bivalent group selected from the group consisting of $CR_{19}R_{20}$, O, S, $NR_{21}$, $SiR_{22}R_{23}$ and CO (wherein each of $R_{19}$ and $R_{20}$ is a hydrogen atom, a $C_{1-12}$alkyl group, a phenyl group, a tolyl group or an anisyl group, and each of $R_{21}$, $R_{22}$ and $R_{23}$ is hydrogen or a methyl group), and n is 0 or 1.

A more preferred phosphite compound among compounds of the formula (5) may, for example, be a phosphite compound of the following formula (10) or (11):

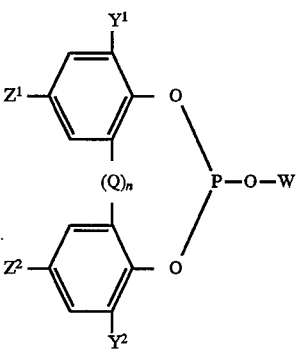

(10)

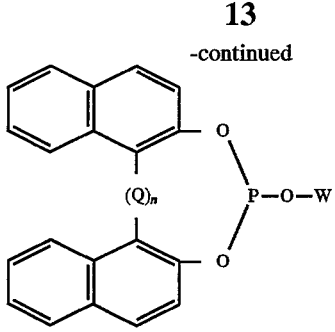

wherein Q is a group of the formula $CR_{24}R_{25}$, wherein each of $R_{24}$ and $R_{25}$ is hydrogen or an alkyl group, W is a substituted or unsubstituted $C_{1-18}$ alkyl group or an aryl group such as a phenyl group or a naphthyl group, which may have a substituent, each of $Z^1$, $Z^2$, $Y_1$ and $Y^2$ is a group selected from the group consisting of hydrogen, $C_{1-8}$ alkyl, aryl, alkaryl, aralkyl, an alicyclic group, a hydroxyl group and a hydrocarbyloxy group. Specific examples of such a compound include the following compounds:

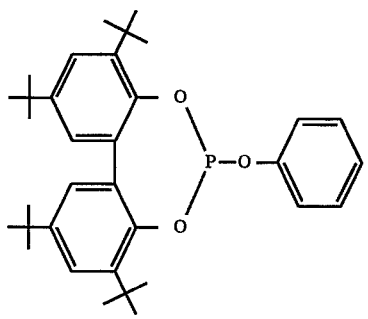

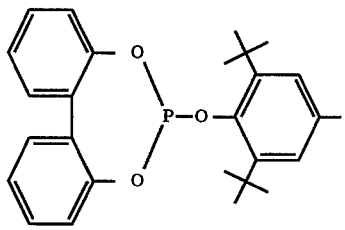

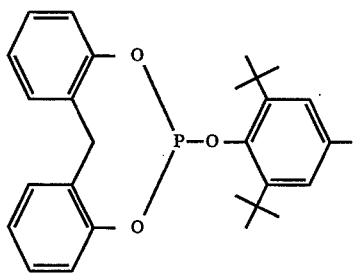

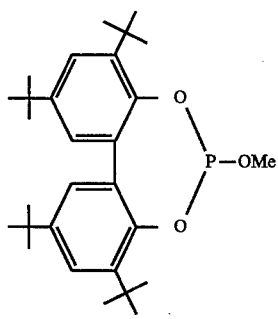

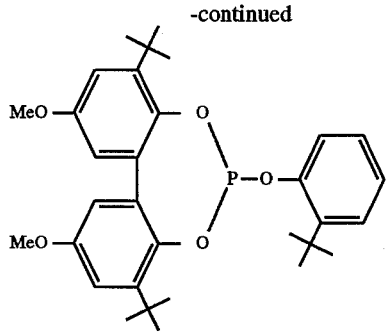

As another example of the phosphite compound having a cyclic structure containing a phosphorous atom in its molecule among phosphite compounds useful in the present invention, a bisphosphite or polyphosphite compound of the following formula (12) may be mentioned.

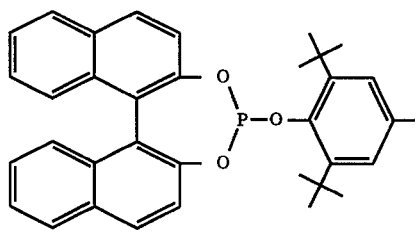

wherein a plurality of Z which may be the same or different, are bivalent organic groups, W is a substituted or unsubstituted m-valent hydrocarbon group, and m is from 2 to 6.

A preferred phosphite compound may, for example, be a phosphite compound of the following formula (13), i.e. a compound of the formula (12) wherein Z is as defined in the above formula (7), (8) or (9), or the respective Z are represented by a combination of such above-mentioned formulas.

wherein each substituent is as defined in the above-mentioned formula (7), (8) and (9), the respective Z may be the same or different, W is a substituted or unsubstituted m-valent hydrocarbon group, and each of R groups which are independent of one another, is a group selected from the group consisting of substituted and unsubstituted monovalent hydrocarbon groups such as alkyl, aryl, alkaryl, aralkyl and alicyclic groups, each of $m_1$, $m_2$ and $m_3$ is from 0 to 6, provided that $m_1+m_2+m_3$ is from 2 to 6, and m is equal to $m_1+m_2+m_3$.

A more preferred phosphite compound is a phosphite compound of the formula (12) wherein Z is as defined in the above formula (9).

A still more preferred phosphite compound may, for example, be a phosphite compound of the formula (12) wherein Z is as defined in the above formula (10) and/or (11). Specific examples of such a compound include the following compounds:

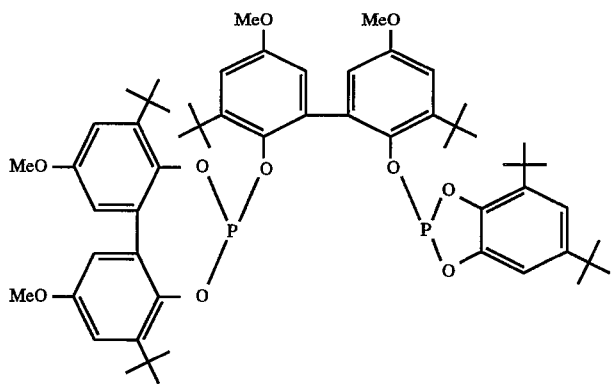

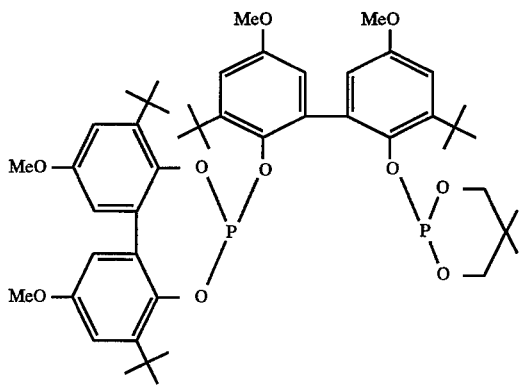

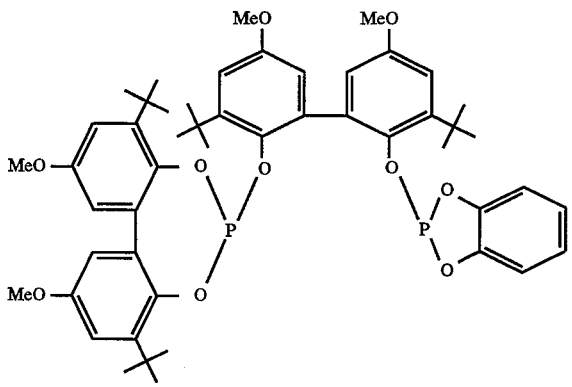

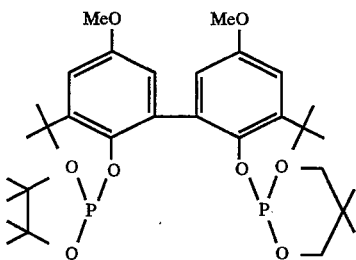

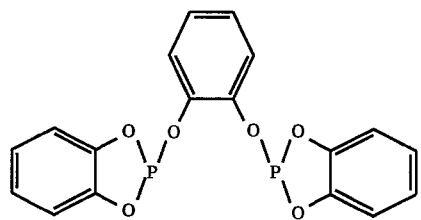
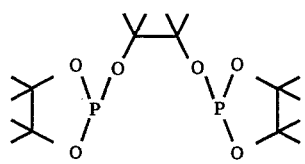
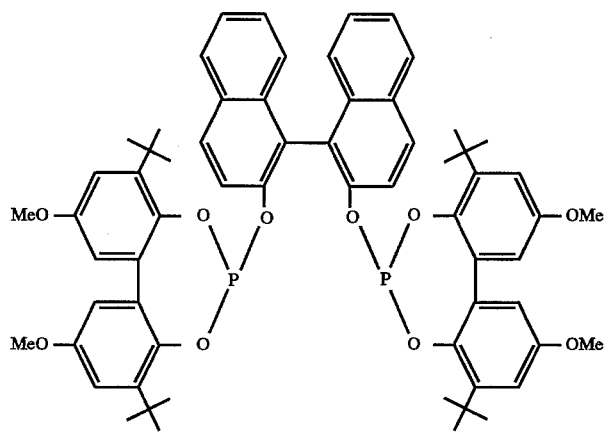
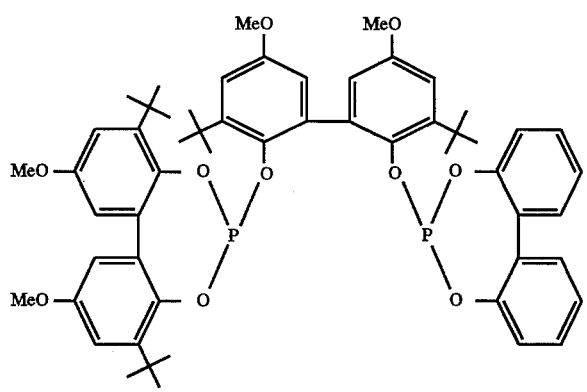
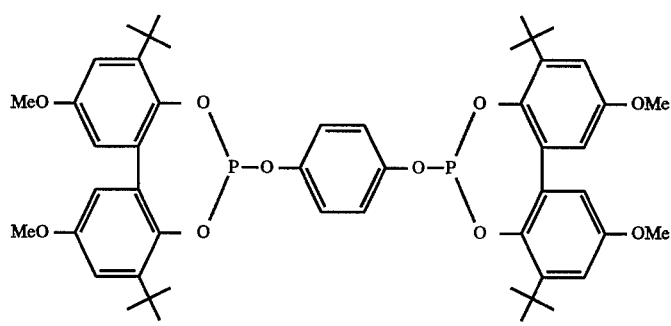

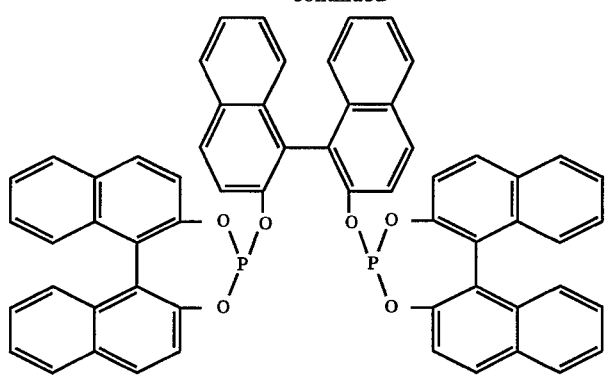
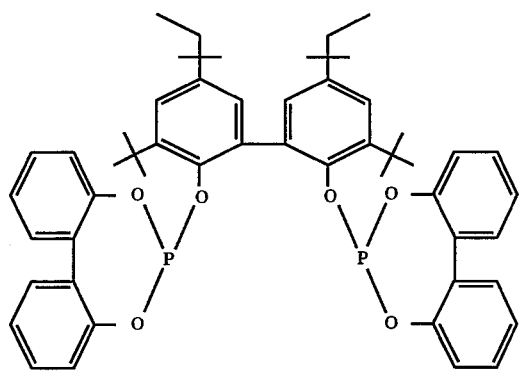
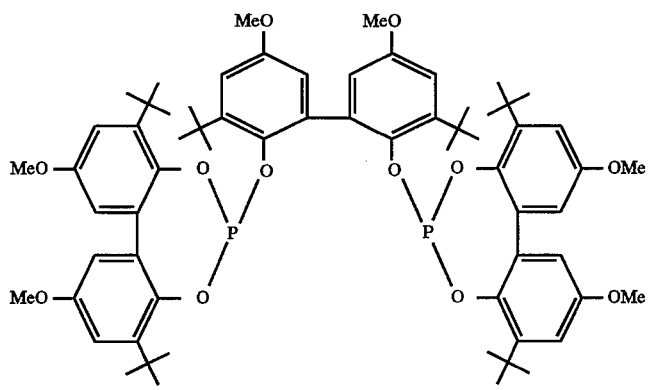
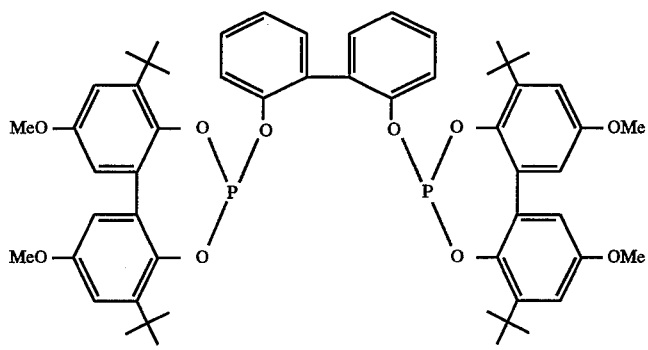

-continued

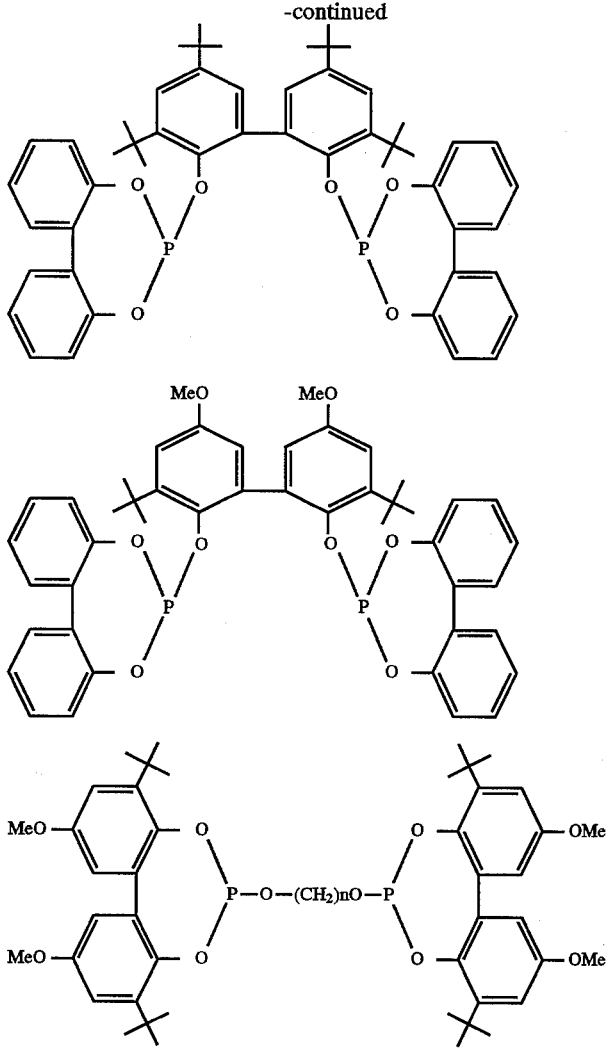

Among phosphite compounds useful in the present invention, a polyphosphite having a cyclic structure containing a phosphorus atom in its molecule may, for example, be a phosphite compound of the following formula (14):

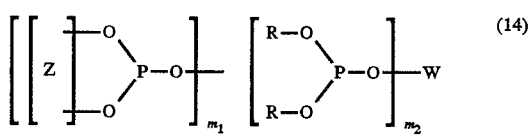
(14)

wherein W is a substituted or unsubstituted m-valent hydrocarbon group, Z is a bivalent organic group like in the formula (5), the plurality of Z may be the same or different from one another, each R is a substituted or unsubstituted monovalent hydrocarbon group, and each of $m_1$ and $m_2$ is from 1 to 6, provided that $m_1+m_2$ is 2 to 6, and m is equal to $m_1 +m_2$.

A preferred phosphite compound is a phosphite compound of the formula (14) wherein Z is as defined in the above formula (7), (8) or (9), or the plurality of Z are represented by a combination of such above-mentioned formulas.

A more preferred phosphite compound may be a phosphite compound of the following formula (15) or (16) i.e. a compound of the formula (14) wherein Z is as defined in the above formula (10) or (11), or the plurality of Z are a combination of such above-mentioned formulas.

(15)

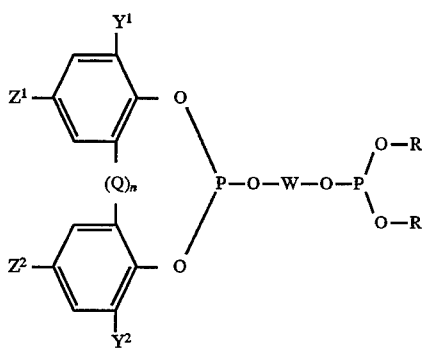

(16)

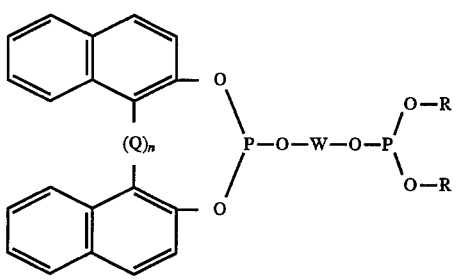

wherein W is a substituted or unsubstituted bivalent hydrocarbon group selected from the group consisting of alkylene, arylene and arylene-$(CH_2)_2$—$(Q)_n$—$(CH_2)_2$-arylene-(each arylene group may have a substituent), Q is a bivalent group selected from the group consisting of $CR_{26}R_{27}$, O, S, $NR_{28}$, $SiR_{29}R_{30}$ and CO (wherein each of $R_{26}$ and $R_{27}$ is hydrogen or an alkyl group, and each of $R_{28}$, $R_{29}$ and $R_{30}$ is hydrogen or a methyl group), and n is 0 or 1, and R is a substituted or unsubstituted hydrocarbon group such as an alkyl group, an aryl group, an alkaryl group, an aralkyl group or an alicyclic group. Specific examples of such a compound include the following compounds:

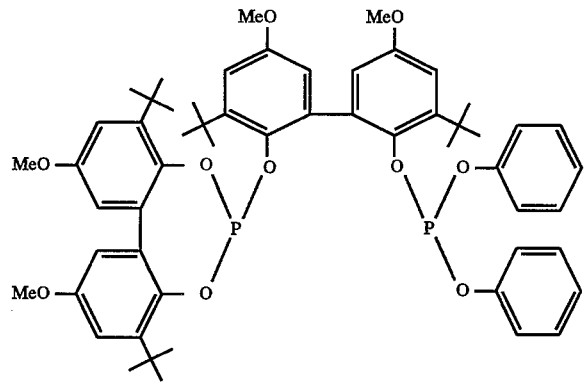

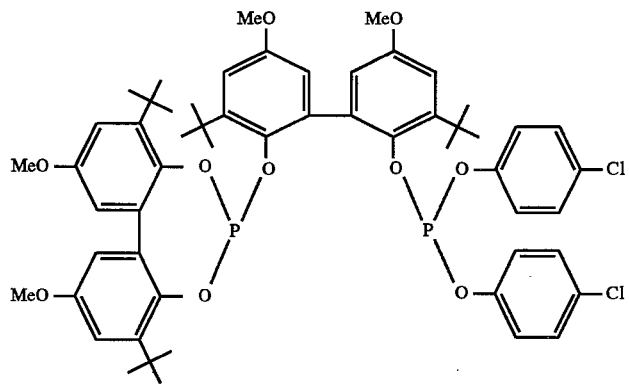

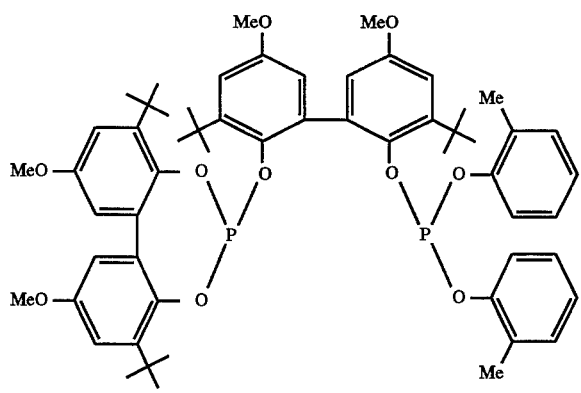
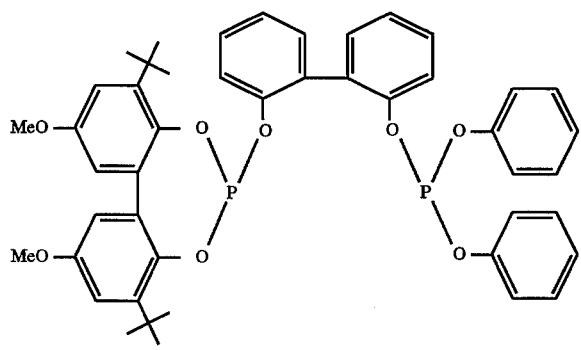
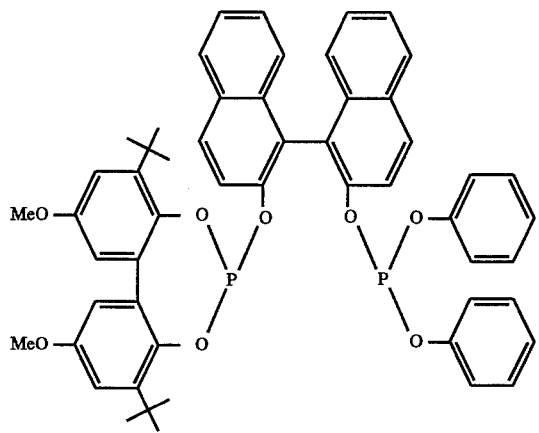
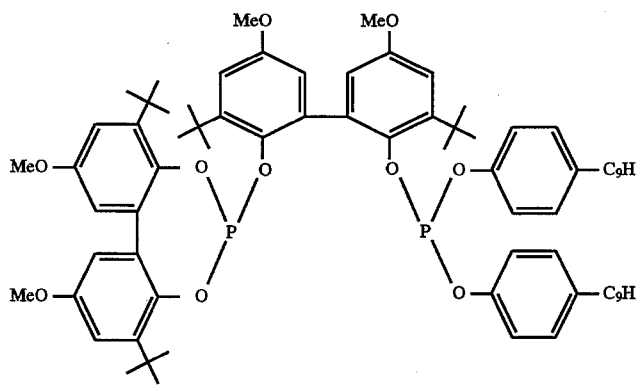

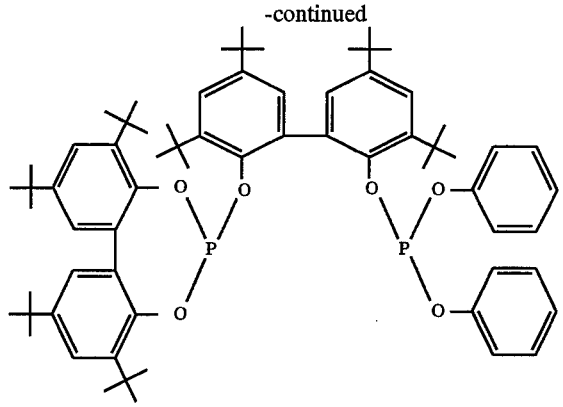

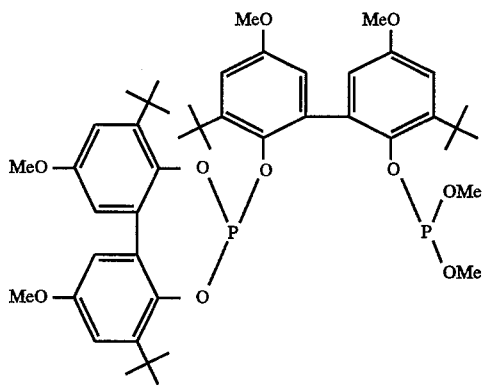

As a phosphite compound to be used in the present invention, a compound may be employed which has a phosphite structure as a partial structure and a partial structure having a coordinating ability such as a phosphine structure in the same molecule.

The partial structure having a coordinating ability may be the one having an unpaired electron pair such as —$PR_{31}R_{32}$, —$OPR_{31}R_{32}$, —$P(O)(OR_{31})$, —$NR_{31}R_{32}$, —$NR_{31}C(O)R_{32}$ or —$SR_{31}$, wherein each of $R_{31}$ and $R_{32}$ which may be the same or different, is hydrogen or a monovalent hydrocarbon group, or $R_{31}$ and $R_{32}$ together form a ring structure.

Preferred among them is a phosphite compound which has the above-mentioned partial structure having a coordinating ability, as $R_1$, $R_2$ or $R_3$ in the above-mentioned formula (1), as $A_1$ in the above-mentioned formula (4), or as the substituent for W in the above-mentioned formula (5), (12) or (14). Specific examples of such a phosphite compound include the following compounds:

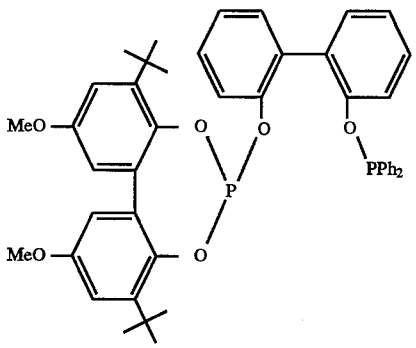

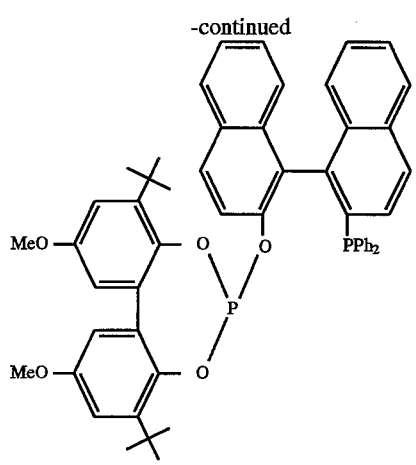

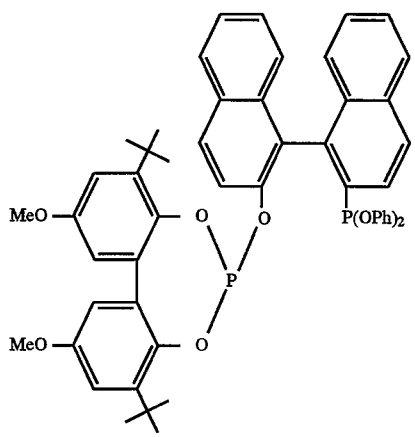

-continued

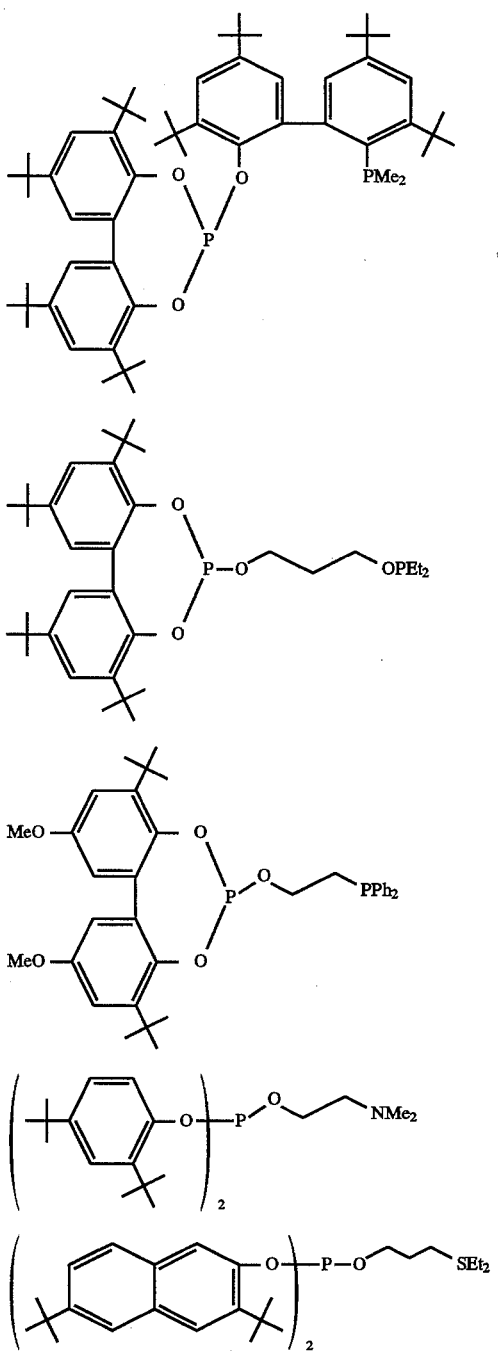

A free phosphite ligand present in the hydroformylation process employed in the present invention, may be present in any excess amount. For example, it is usually at least 1 mol per mol of a Group 8 metal present in the reaction medium, and it may be present up to 100 mols or even more. In general, the sum of the (complex forming) phosphite bonded to a Group 8 metal and the free (non-complex forming) phosphite present in the reaction medium may be from about 4 to about 500 mols per mol of a Group 8 metal for most purposes. Further, to maintain a predetermined amount of free ligand in the reaction medium, a supplemental phosphite ligand may be supplied to the reaction medium in an optional manner. It is usual to employ a ligand of the same type for both the free phosphite ligand and the phosphite ligand for a Group 8 metal-phosphite complex catalyst. However, if necessary, different phosphite ligands may be used for the respective purposes, or a mixture of two or more different phosphite ligands may be used.

The amount of the Group 8 metal-phosphite complex catalyst present in the reaction medium for the hydroformylation process of the present invention may be the minimum amount required to bring about a predetermined Group 8 metal concentration to be employed and may be at least an amount satisfying the standard relating to a catalytic amount of Group 8 metal. When rhodium is used as the Group 8 metal, the rhodium concentration in the hydroformylation reaction medium is usually sufficient at a level within a range of from 1 ppm to 1000 ppm, as calculated as metal rhodium, and it is preferred to employ a rhodium concentration of from 10 to 500 ppm, more preferably from 25 to 350 ppm.

The olefinic unsaturated compound to be used in the present invention may be a single substance or a mixture, and it may have a straight chain, branched chain or cyclic structure. A preferred olefinic unsaturated compound is a $C_{2-20}$ olefin, which may contain two or more ethylenically unsaturated groups. Further, it is preferred to use an olefin which has low solubility in the extraction solution to be used in the present invention. It may contain a carbonyl group, a carbonyloxy group, a hydrocarbyloxy group, a hydroxyl group, an oxycarbonyl group, a halogen atom, an alkoxy group, an aryl group, an alkyl group or a haloalkyl group which presents substantially no adverse effect to the hydroformylation reaction.

The olefinic unsaturated compound includes, for example, an α-olefin, an internal olefin, an alkylalkenoic acid, an alkenylalkanoic acid, an alkenylalkyl ether and an alkenol. Specifically, it includes, for example, olefinic hydrocarbons such as ethylene, propylene, butene, pentene, hexene, octene, nonene, decene, dodecene, octadecene, cyclohexene, a mixture of propylene dimers, a mixture of propylene trimers, a mixture of propylene tetramers, a mixture of butene dimers, a mixture of butene trimers, styrene, 3-phenyl-1-propene, 1,4-hexadiene, 1,7-octadiene and 3-cyclohexyl-1-butene, allyl alcohol, 1-hexen-4-ol, 1-octen-4-ol, vinyl acetate, allyl acetate, 3-butenyl acetate, allyl propionate, allyl acetate, methyl methacrylate, 3-butenyl acetate, vinyl ethyl ether, vinyl methyl ether, allyl ethyl ether, n-propyl-7-octenoate, 3-butenenitrile, and 5-hexeneamide. Among them, olefinic hydrocarbons are preferred. More preferred are monoolefins. Among monoolefins, propylene and butene are most preferred.

As the reaction medium for the hydroformylation reaction, an aromatic hydrocarbon such as benzene, toluene or xylene, or other solvents for reaction may be used, or the feed olefin itself may be used, or a mixture of two or more solvents may be employed. Usually, it is preferred to employ the aldehyde product and/or a high boiling aldehyde liquid condensation by-product formed in the reaction system. For example, even when an optional primary solvent is employed at the initial stage of a continuous process, by the nature of the continuous process, the primary solvent usually finally becomes to be composed of the aldehyde product and a high boiling aldehyde liquid condensation by-product. If desired, such an aldehyde condensation by-product may preliminarily be formed. The amount of the solvent is not critical to the present invention, and the solvent may be in an amount sufficient to maintain a specific metal complex catalyst concentration desired for the predetermined process and to perform the role as the reaction medium. The amount of the solvent is usually from about 5 to about 95 wt %, based on the total weight of the reaction medium. In the present invention, from the viewpoint of the two-phase separation for the subsequent extraction, the solvent for reaction preferably has a density differing by at least 0.05 g/ml from the density of the extraction solvent to be used, and it is preferred to use a water-insoluble solvent or non-polar solvent. In a case of a certain solvent for the hydroformylation reaction, it will be necessary to use an extraction solution consisting of a combination of a specific solvent and water in a specific ratio to attain satisfactory phase separation.

As a hydroformylation reaction condition, it is preferred to operate the hydroformylation process under total gas pressure of hydrogen, carbon monoxide and the olefinic unsaturated compound of less than 500 kg/cm$^2$G, more preferably less than 200 kg/cm$^2$G. The lower limit of the total gas pressure is defined by the amounts of the reactants necessary to accomplish the initial rate of the reaction. Further, the carbon monoxide partial pressure in the hydroformylation reaction of the present invention is preferably from 0.1 to 100 kg/cm$^2$, more preferably from 1 to 7 kg/cm$^2$, and the hydrogen partial pressure is preferably from 0.1 to 100 kg/cm$^2$, more preferably from 1 to 8 kg/cm$^2$. In general, the molar ratio of hydrogen to carbon monoxide gas ($H_2$:CO) is from 1:10 to 100:1, preferably from 1:1 to 10:1. The reaction can usually be carried out at a temperature of from room temperature to 150° C., and a reaction temperature within a range of from 50° to 120° C. is preferred for most of the olefin starting materials. At a reaction temperature substantially exceeding 120° C., no substantial merit will be observed, and a deterioration of the catalytic activities is expected as disclosed in Japanese PCT Publication No. 501268/1986, such being usually undesirable.

The hydroformylation reaction of an olefin is usually carried out under the above-mentioned hydroformylation reaction conditions by continuously supplying an olefinic unsaturated compound as starting material, oxo gas (carbon monoxide-hydrogen mixed gas) and a catalyst solution to a continuous type reactor.

A high boiling by-product is formed mainly by a secondary side reaction of aldehyde formed by the hydroformylation reaction. For example, in a hydroformylation reaction of propylene, straight chain n-butyraldehyde and branched chain isobutyraldehyde will be formed. These aldehyde products are highly reactive and tend to undergo polymerization or condensation slowly in the presence of the catalyst even at a relatively low temperature, to form high boiling polycondensation products.

Such high boiling polycondensation products may be, in the case of n-butyraldehyde, a dimer and a trimer as its self polymerization product, 2-ethylhexenal as a condensed dimer, and 2-ethylhexanal and 2-ethylhexanol as its hydrogenation products, n-butanol as a hydrogenated product of n-butyraldehyde, or dibutylacetal of n-butyraldehyde. Further, also from isobutyraldehyde, the dimer and trimer will be formed as self condensed products by reactions similar to those of n-butyraldehyde. Furthermore, interpolymerization products of n-butyraldehyde and isobutyraldehyde, a dimer, a trimer and derivatives thereof will be formed. In the hydroformylation reaction, a high boiling by-product having a boiling point higher than the phosphite compound to be used in the present invention will also be formed by side reactions.

Now, the present invention will be described in further detail with reference to Examples and Comparative Examples. However, it should be understood that the present invention is by no means restricted to such specific Examples.

EXAMPLES 1 TO 19

[Rh(OAc)(COD)]$_2$ and a phosphite compound of the following formula (A) were dissolved in toluene, and a precarbonylation reaction was carried out at 80° C. for one hour under an oxo gas pressure of 10 kg/cm$^2$G. To this precarbonylated catalyst solution, a high boiling by-product obtained by the following experiment, and n-butanol which is expected to be formed in the reaction system, were added to obtain a model catalyst solution.

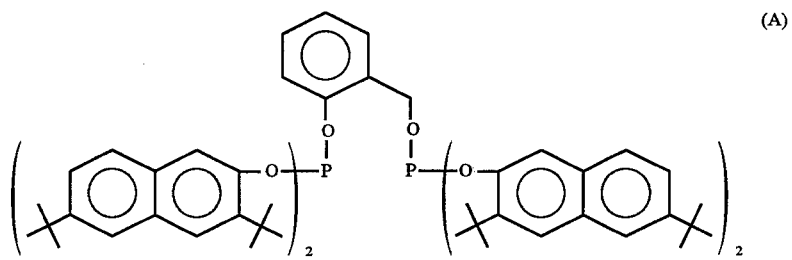

(A)

The added high boiling by-product was obtained by a process for producing butyraldehyde, wherein propylene is hydroformylated in a stirred tank type reactor at 100° C. under a pressure of 17 kg/cm$^2$G using toluene as a solvent and a catalyst solution containing 25 wt % of triphenyl phosphine and rhodium acetate at a rhodium concentration of 300 mg/l. After separating oxo gas and unreacted propylene from the reaction product solution, the aldehyde product was separated by continuous distillation under a pressure of 490 mmHg at a distillation still temperature of 119° C., and the catalyst solution was recycled to the hydroformylation reaction step. By this process, recycling was repeated 32 times, and from the catalyst solution thereby obtained, the solvent was removed by continuous distillation under a pressure of 70 mmHg at a distillation still temperature of 150° C. Then, steam distillation was further continuously carried out under a pressure of 30 mmHg at a distillation still temperature of 153° C., to obtain a high boiling by-product composed mainly of dimmers and trimmers of aldehyde.

The composition of the prepared model catalyst solution was as follows.

Rh: 50 mg/l phosphite compound (A): 0.2 wt % n-Butanol: 2.1 wt %

High boiling by-product: 48.6 wt %

Toluene: 49.3 wt %

Using this model catalyst solution, an extraction test was carried out. The volume ratio of the extraction solution to the model catalyst solution was 1:1. The extraction temperature was 25° C., and the shaking time after mixing the catalyst solution and the extraction solution, was 30 minutes. Then, the mixture was left to stand from 30 minutes to 150 minutes. In most cases, the mixture separated into two phases within 60 minutes. The complex catalyst and the high boiling by-product in the hydroformylation reaction solution layer and the extraction solution layer were, respectively, analyzed, and the Kp value of the complex catalyst (complex) and the Kp value of the high boiling by-product (high boiling) were obtained. The results are shown in Table 1.

TABLE 1

| Examples | Extraction solution (ratio to water) | Kp (complex) | Kp (high boiling) |
| --- | --- | --- | --- |
| 1 | Acetic acid/water (4/1) | 0.011 | 0.234 |
| 2 | Acetic acid/water (2.5/1) | 0.011 | 0.234 |
| 3 | Acetic acid/water (1/1) | 0.011 | 0.234 |
| 4 | Ethylene glycol (—) | 0.003 | 0.018 |
| 5 | 1,4-butanediol | 0.004 | 0.181 |
| 6 | Ethanol/water (2.7/1) | 0.008 | 0.065 |
| 7 | Methanol/water (4/1) | 0.022 | 0.232 |
| 8 | Methanol/water (2.5/1) | 0.001 | 0.056 |
| 9 | Methanol/water (1/1) | 0.000 | 0.007 |
| 10 | Dimethylformamide/water (4/1) | 0.010 | 0.089 |
| 11 | N-methylpyrrolidone/water (4/1) | 0.005 | 0.083 |
| 12 | Formic acid/water (4/1) | 0.007 | 0.057 |
| 13 | Sulfolane/water (4/1) | 0.018 | 0.052 |
| 14 | Acetonitrile/water (4/1) | 0.029 | 0.000 |
| 15 | Methyl ethyl ketone/water (4/1) | 0.084 | 0.000 |
| 16 | Acetone/water (4/1) | 0.002 | 0.000 |
| 17 | Diethyl ether (4/1) | 0.018 | 0.000 |
| 18 | Dioxane/water (4/1) | 0.023 | 0.000 |

Examples 1 to 13 are examples wherein the high boiling by-product was selectively extracted, as compared with the complex catalyst. Whereas, Examples 14 to 18 are examples wherein the complex catalyst was selectively extracted. In this case, the catalyst component was recovered from the extraction solution layer by reverse extraction, and from the hydroformylation reaction solution containing the high boiling by-product, the majority of the toluene solvent was recovered by distillation. In the above operations, no decomposition of the phosphite was observed.

EXAMPLES 19 AND 20

The extraction test was carried out in the same manner as in Examples 1 to 18 except that the volume ratio of the polar solvent (methanol) to water was changed to 4:1, and the volume ratio of the extraction solution to the catalyst solution was changed as shown in Table 2. In each operation, no decomposition of the phosphite was observed. The results are shown in Table 2.

TABLE 2

| Examples | Extraction solvent | Volume ratio | Kp (complex) | Kp (high boiling) |
| --- | --- | --- | --- | --- |
| 19 | Methanol | 2 | 0.008 | 0.458 |
| 20 | Methanol | 0.67 | 0.005 | 0.109 |

EXAMPLE 21

[Rh(OAc)(COD)]$_2$ and a phosphite compound of the formula (B) were dissolved in toluene, so that the rhodium concentration became 100 mg/l, and the molar ratio of P/Rh became 8. To this solution, the same high boiling by-product as used in Examples 1 to 18, was added to obtain a model catalyst solution.

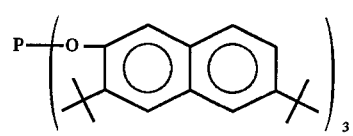

The composition of the obtained model catalyst solution was as follows.

Rh: 50 mg/l phosphite compound (B): 0.4 wt % n-Butanol: 1.87 wt %

High boiling by-product: 48.8 wt %

Toluene: 49.0 wt %

Using this model catalyst solution, a test was carried out under the same extraction conditions as in Examples 1 to 18. In this operation, no decomposition of the phosphite was observed. The results are shown in Table 3.

TABLE 3

| Examples | Extraction solvent | Ratio to water | Kp (complex) | Kp (high boiling) |
| --- | --- | --- | --- | --- |
| 21 | Methanol | 4 | 0.058 | 0.337 |

COMPARATIVE EXAMPLE 1

A model catalyst solution was prepared in the same manner as in Example 21 except that instead of the phosphite ligand (B), triphenyl phosphine was used.

The composition of the prepared model catalyst solution was as follows.

Rh: 50 mg/l

Triphenyl phosphine: 4.0 wt % n-Butanol: 1.7 wt %

High boiling by-product: 48.7 wt %

Toluene: 45.6 wt %

Using this model catalyst solution, a test was carried out under the same extraction conditions as in Examples 1 to 18. The results are shown in Table 4

TABLE 4

| Comparative Example | Extraction solvent | Ratio to water | Kp (complex) | Kp (high boiling) |
| --- | --- | --- | --- | --- |
| 1 | Methanol | 4 | 0.257 | 0.264 |

It is evident that in this system, the complex catalyst and the high boiling by-product were extracted in substantially the same ratio, as compared with Examples 7 and 21 wherein the tests were conducted under the same conditions.

According to the method of the present invention, it is possible to suppress the decomposition of the phosphite ligand and to separate a part of the high boiling by-product while minimizing the loss of the catalyst component, even when a phosphite type which is more susceptible to decomposition than the phosphine type, is used for the hydroformylation reaction. Thus, the method of the present invention is industrially useful and advantageous.

What is claimed is:

1. A method for producing aldehydes, which comprises reacting an olefinic unsaturated compound with carbon monoxide and hydrogen in a liquid phase in the presence of a Group 8 metal-phosphite complex catalyst, wherein a reaction product solution containing the complex catalyst and a high boiling by-product, obtained by the reaction, is intimately contacted with an extraction solution containing a polar solvent, to have either the complex catalyst or the high boiling by-product extracted selectively, followed by phase separation to separate a layer of the extraction solution from a layer of the reaction product solution.

2. The method for producing aldehydes according to claim 1, wherein the reaction product solution is intimately contacted with the extraction solution to have the high boiling by-product extracted selectively.

3. The method for producing aldehydes according to claim 2, wherein the extraction solution contains an alkanol, a carboxylic acid, a diol or an amide.

4. The method for producing aldehydes according to claim 2, wherein the complex catalyst has a distribution coefficient Kp of at most 0.03.

5. The method for producing aldehydes according to claim 1, wherein the reaction product solution is intimately contacted with the extraction solution to have the complex catalyst extracted selectively.

6. The method for producing aldehydes according to claim 5, wherein the extraction solution contains an amine, a nitrile, a ketone or an ether.

7. The method for producing aldehydes according to claim 1, wherein the extraction solution contains water.

8. The method for producing aldehydes according to claim 7, wherein the polar solvent is not water and wherein the ratio of the polar solvent to the water is within a range of from 5:1 to 1:1.

9. The method for producing aldehydes according to claim 1, wherein the volume ratio of the extraction solution to the reaction product solution is within a range of from 1:1 to 1:4.

10. The method for producing aldehydes according to claim 1, wherein the intimate contact of the reaction product solution with the extraction solution is carried out within a temperature range of from 10° to 45° C.

11. The method for producing aldehydes according to claim 1, wherein the olefinic unsaturated compound is an olefinic hydrocarbon.

12. The method for producing aldehydes according to claim 11, wherein the olefinic unsaturated compound is propylene or butenes.

13. The method for producing aldehydes according to claim 1, wherein the phosphite compound of the complex catalyst is a phosphite compound having no cyclic structure containing a phosphorus atom in its molecule, and at least one alcohol component of the phosphite compound is an aromatic alcohol which has a hydroxyl group directly bonded to an aromatic ring and which has a hydrocarbon substituent on a carbon atom adjacent to the carbon atom to which the hydroxyl group is bonded.

* * * * *